US008501819B2

(12) United States Patent
Alonso et al.

(10) Patent No.: US 8,501,819 B2
(45) Date of Patent: *Aug. 6, 2013

(54) STABILIZED COMPOSITIONS OF VOLATILE ALKYLATING AGENTS AND METHODS OF USING THEREOF

(75) Inventors: Robert Alonso, Wayne, PA (US); Peter A. Crooks, Little Rock, AR (US); Mark A. Pimley, West Chester, PA (US)

(73) Assignee: Ceptaris Therapeutics, Inc., Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/948,593

(22) Filed: Nov. 17, 2010

(65) Prior Publication Data

US 2011/0065803 A1    Mar. 17, 2011

Related U.S. Application Data

(62) Division of application No. 12/549,258, filed on Aug. 27, 2009, now Pat. No. 7,838,564, which is a division of application No. 11/369,305, filed on Mar. 7, 2006, now Pat. No. 7,872,050.

(60) Provisional application No. 60/661,356, filed on Mar. 14, 2005, provisional application No. 60/751,128, filed on Dec. 16, 2005.

(51) Int. Cl.
*A01N 33/02* (2006.01)
*A61K 31/13* (2006.01)

(52) U.S. Cl.
USPC .......................................... 514/672; 424/400

(58) Field of Classification Search
USPC .......................................... 514/672; 424/400
See application file for complete search history.

(56) References Cited

U.S. PATENT DOCUMENTS

| | | |
|---|---|---|
| 3,767,792 A | 10/1973 | Cook et al. |
| 3,904,766 A | 9/1975 | Van Scott et al. |
| 4,083,692 A | 4/1978 | Epstein et al. |
| 4,206,222 A | 6/1980 | Valetas |
| 4,725,438 A | 2/1988 | Leazer |
| 4,853,388 A | 8/1989 | Pearlman |
| 4,863,910 A | 9/1989 | Takayanagi |
| 4,888,344 A | 12/1989 | Sunagawa et al. |
| 4,888,354 A | 12/1989 | Chang et al. |
| 4,949,641 A | 8/1990 | Sayles |
| 5,051,363 A | 9/1991 | Ritter et al. |
| 5,229,422 A | 7/1993 | Takahashi et al. |
| 5,326,790 A | 7/1994 | Thornfeldt |
| 5,616,332 A | 4/1997 | Herstein |
| 5,719,197 A | 2/1998 | Kanios et al. |
| 5,744,460 A | 4/1998 | Muller et al. |
| 5,820,872 A | 10/1998 | Edelson et al. |
| 5,824,650 A | 10/1998 | De Lacharriere et al. |
| 5,948,437 A | 9/1999 | Parikh et al. |
| 5,972,892 A | 10/1999 | De Lacharriere et al. |
| 6,005,002 A | 12/1999 | Springer et al. |
| 6,017,902 A | 1/2000 | Glass et al. |
| 6,124,108 A | 9/2000 | Ray |
| 6,255,502 B1 | 7/2001 | Penkler et al. |
| 6,329,148 B1 | 12/2001 | Rosen et al. |
| 6,472,435 B1 | 10/2002 | Boyle |
| 6,692,742 B1 | 2/2004 | Nakamura et al. |
| 6,753,155 B1 | 6/2004 | Ray |
| 7,323,171 B2 | 1/2008 | Wallner et al. |
| 7,470,433 B2 | 12/2008 | Carrara et al. |
| 7,838,564 B2 | 11/2010 | Alonso et al. |
| 2001/0049349 A1 | 12/2001 | Chinery et al. |
| 2002/0142028 A1 | 10/2002 | Elliesen et al. |
| 2002/0146692 A1 | 10/2002 | Yamazaki et al. |
| 2003/0083321 A1 | 5/2003 | Lerner et al. |
| 2003/0087961 A1 | 5/2003 | Ko et al. |
| 2003/0215471 A1 | 11/2003 | Wilmott et al. |
| 2005/0039228 A1 | 2/2005 | Ding et al. |
| 2006/0079492 A1 | 4/2006 | Ahlem et al. |
| 2006/0205694 A1 | 9/2006 | Alonso et al. |
| 2006/0281720 A1 | 12/2006 | Loria |
| 2007/0287719 A1 | 12/2007 | Boyden et al. |
| 2008/0194699 A1 | 8/2008 | Alonso et al. |
| 2009/0247645 A1 | 10/2009 | Alonso et al. |
| 2009/0312290 A1 | 12/2009 | Panasci et al. |
| 2010/0029783 A9 | 2/2010 | Alonso et al. |
| 2010/0152300 A1 | 6/2010 | Alonso et al. |
| 2011/0039943 A1 | 2/2011 | Alonso et al. |

FOREIGN PATENT DOCUMENTS

| | | |
|---|---|---|
| EP | 0317281 | 5/1989 |
| WO | WO 87/04154 | 7/1987 |
| WO | WO 99/42578 A2 | 8/1999 |
| WO | WO 99/42578 A3 | 12/1999 |
| WO | WO 03/037380 | 8/2003 |
| WO | WO 2004/050057 | 6/2004 |
| WO | WO 2005/007129 A2 * | 1/2005 |
| WO | WO 2005/007129 A3 | 8/2005 |
| WO | WO 2006/099385 | 9/2006 |
| WO | WO 2009/120493 | 10/2009 |

OTHER PUBLICATIONS

Non-final office action mailed on Jan. 27, 2011 in connection with U.S. Appl. No. 11/908,531.
Arrazola et al., "Treatment of alopecia areata with topical nitrogen mustard," Int J Dermatol 24(9):608-10, 1985.
Bell, "The effect of the solvent on protolytic equilibria," The Proton in Chemistry, Second Edition (Cornell University Press) pp. 44-55, 1959.

(Continued)

*Primary Examiner* — Kendra D Carter
(74) *Attorney, Agent, or Firm* — Wilson Sonsini Goodrich & Rosati

(57) ABSTRACT

A composition and method for treatment of cancer. The composition for treating a skin disorder, comprising: a Nitrogen Mustard or an HX salt of the Nitrogen Mustard, wherein the Nitrogen Mustard or the HX salt of the Nitrogen Mustard is in a non-aqueous vehicle or carrier that does not include petrolatum or ethanol does not include petrolatum or ethanol. The method comprises topically applying the composition of a Nitrogen Mustard or a HX salt of the Nitrogen Mustard to the affected skin, wherein the Nitrogen Mustard or the HX salt of the Nitrogen Mustard is in a non-aqueous vehicle or carrier that does not include petrolatum or ethanol.

10 Claims, 3 Drawing Sheets

(56) References Cited

OTHER PUBLICATIONS

Bernardo et al., "Topical nitrogen mustard in the treatment of alopecia areata: a bilateral comparison study," J Am Acad Dermatol 49(2):291-4, 2003.

Bonina et al., "Vehicle effects on in vitro skin permeation of and stratum corneum affinity for model drugs caffeine and testosterone," Int J Pharmaceutics, 100:41-47, 1993.

Chabner et al., "Antineoplastic agents," Goodman & Gilman's The Pharmacological Basis of Therapeutics, Tenth Edition, Chapter 52, pp. 1389-1397, 2001.

Connors et al., "Mechlorethamine," Chemical Stability of Pharmaceuticals. A Handbook for Pharmacists, Second Edition (John Wiley & Sons, Inc.) pp. 529-533, 1986.

Cummings et al., "The long term stability of mechlorethamine hydrochloride (nitrogen mustard) ointment measured by HPLC," J Pharm Pharmacol 45:6-9, 1993.

Final office action mailed on Jul. 6, 2010 in connection with U.S. Appl. No. 11/908,531.

Foulec et al., "Evaluation of a 1-h exposure time to mechlorethamine in patients undergoing topical treatment", Brit. J. Derm. 147, 926-930 (2002).

Khan et al., "Hepatocyte toxicity of mechlorethamine and other alkylating anticancer drugs. Role of lipid peroxidation," Biochem Pharmacol 43(9):1963-7 (1992).

Kim et al., "Topical Nitrogen Mustard in the Management of Mycosis Fungoides," Arch Dermatol. 2003;139:165-173.

Kravitz et al., "Topical nitrogen mustard induced carcinogenesis," Acta Derm Venereol, 1978 (abstract).

Lessin et al., "Testing efficacy and safety of topical nitrogen mustard in mycosis fungoides," submitted to 21$^{st}$ World Congress of Dermatology in Buenos Aires, Oct. 1-5, 2007.

Lessin, "Nitrogen mustard (NM) ointment formulation containing propylene glycol (PG) is active in treating mycosis fungoides (MF)," J Inv Dermatol, 2007 (abstract).

Mechlorethamine (Topical), Drugs.com, Drug information online www.drugs.com/mmx/mechlorethamine-hydrochloride.html, Jun. 14, 2010.

Non-final office action mailed Dec. 24, 2009 in U.S. Appl. No. 11/369,305.

Non-final office action mailed Feb. 19, 2010 in U.S. Appl. No. 11/908,531.

Non-final office action mailed Jun. 10, 2010 in U.S. Appl. No. 12/549,258.

PCT/US2006/009060 International Search Report mailed Jan. 28, 2008.

PCT/US2009/036737 International Search Report mailed Jan. 11, 2010.

Price, "Ointment-based mechlorethamine treatment for mycosis fungoides," cancer 52:2214-2219, 1983.

Ritschel, et al., "Stability of the nitrogen mustard mechlorethamine in novel formulations for dermatological use," Int'l J. Pharm., 362:67-73, 2008.

Tang et al., "Topical mechlorethamine restores autoimmune-arrested follicular activity in mice with an alopecia areata-like disease by targeting infiltrated lymphocytes," J Invest Dermatol 120(3):400-6, 2003.

Taylor et al. "Mechlorethamine hydrochloride solutions and ointment prolonged stability and biological activity," Archives of Dermatology, Jul. 1980, vol. 116(7), pp. 783-785.

Wormser et al., "Noninvasive procedure for in situ determination of skin surface aspartic proteinase activity in animals; implications for human skin," Arch Dermatol Res, 289: 686-691, 1997.

Wu et al., "Elucidation of the chemical structures of natural antioxidants isolated from rosemary," JAOCS 59(8):339-345 (1982).

European search report and opinion dated Mar. 31, 2008 for EP Application No. 06738150.9.

U.S. Appl. No. 13/300,021, filed Nov. 18, 2011, Alonso et al.

Morissette, et al. High-throughput crystallization: polymorphs, salts, co-crystals and solvates of pharmaceutical solids. Advanced Drug Delivery Reviews. 2004; 56:275-300.

Ash, et al. Handbook of preservatives. Synapse Information Resources, Inc. 2004, pp. 292, 294 and 379.

International search report and written opinion dated Sep. 18, 2012 for PCT/US2012/046155.

Notice of allowance dated Jan. 8, 2013 for U.S. Appl. No. 11/908,531.

Notice of allowance dated Oct. 5, 2012 for U.S. Appl. No. 11/908,531.

Notice of allowance dated Oct. 23, 2012 for U.S. Appl. No. 12/687,605.

Novoembichin compound summary. PubMed. Http://pubchem.ncbi.nlm.nih.gov/summary/summary.cgi?cid=121547. Obtained Aug. 8, 2012.

Office action dated Mar. 8, 2012 for U.S. Appl. No. 11/908,531.
Office action dated May 18, 2012 for U.S. Appl. No. 12/687,605.
Office action dated Aug. 16, 2012 for U.S. Appl. No. 12/401,812.
Office action dated Aug. 31, 2011 for U.S. Appl. No. 11/908,531.
Office action dated Oct. 9, 2012 for U.S. Appl. No. 12/890,183.
Office action dated Nov. 3, 2011 for U.S. Appl. No. 12/687,605.
Office action dated Dec. 21, 2011 for U.S. Appl. No. 12/401,812.

Quatrebarbes, et al. Treatment of early-stage mycosis fungoides with twice-weekly applications of mechlorethamine and topical corticosteroids: a prospective study. Arch Dermatol. Sep. 2005;141(9):1117-20.

Reepmeyer, C. Analysis of the nitrogen mustard mechlorethamine in topical pharmaceutical preparations by high-performance liquid chromatography. J Chromatogr A. Sep. 2, 2005;1085(2):262-9.

\* cited by examiner

STABILIZED COMPOSITIONS OF VOLATILE ALKYLATING AGENTS AND METHODS OF USING THEREOF

The present patent application is a division of U.S. application Ser. No. 12/549,258, filed Aug. 27, 2009, now U.S. Pat. No. 7,838,564, which is a division of U.S. application Ser. No. 11/369,305, filed Mar. 7, 2006, now U.S. Pat. No. 7,872,050, which is a non-provisional application claiming priority from provisional applications with Ser. Nos. 60/661,356 (filed Mar. 14, 2005 and titled "Stabilized Compositions of Volatile Alkylating Agents and Methods of Using Thereof) and 60/751,128 (filed Dec. 16, 2005 and also titled "Stabilized Compositions of Volatile Alkylating Agents and Methods of Using Thereof).

1. FIELD OF THE INVENTION

The present invention relates generally to a composition and method for topical treatment of skin disease, and more specifically to a stabilized Nitrogen Mustard composition and method for topically treating the skin disease.

BACKGROUND

Cutaneous T-cell lymphoma (CTCL) is a malignancy of the T-helper (CD4+) cells of the immune system. CTCL, also known as mycosis fungoides (MF), is a cancer of the white blood cells that primarily affects the skin and only secondarily affects other sites. This disease involves the uncontrolled proliferation of T-lymphocytes known as T-helper cells, so named because of their role in the immune response. T-helper cells are characterized by the presence of a protein receptor on their surface called CD4. Accordingly, T-helper cells are said to be CD4+.

The proliferation of T-helper cells results in the penetration, or infiltration, of these abnormal cells into the epidermal layer of the skin. The skin reacts with slightly scaling lesions that itch, although the sites of greatest infiltration do not necessarily correspond to the sites of the lesions. The lesions are most often located on the trunk, but can be present on any part of the body. In the most common course of the disease, the patchy lesions progress to palpable plaques that are deeper red and have more defined edges. As the disease worsens, skin tumors develop that are often mushroom-shaped, hence the name mycosis fungoides. Finally, the cancer progresses to extracutanous involvement, often in the lymph nodes or the viscera.

CTCL is a rare disease, with an annual incidence of about 0.29 cases per 100,000 persons in the United States. It is about half as common in Eastern Europe. However, this discrepancy may be attributed to a differing physician awareness of the disease rather than a true difference in occurrence. In the Unites States, there are about 500-600 new cases a year and about 100-200 deaths. CTCL is usually seen in older adults; the median age at diagnosis is 55-60 years. It strikes twice as many men as women. The average life expectancy at diagnosis is 7-10 years, even without treatment.

The most common side effect for treatments applied to the skin is skin hypersensitivity to the drug. There is a need for improved compositions and methods for skin diseases that avoid or minimize skin hypersensitivity to the drug.

SUMMARY OF THE INVENTION

A first aspect of the present invention provides a composition for treating a skin disorder, comprising: a Nitrogen Mustard or an HX salt of the Nitrogen Mustard, wherein the Nitrogen Mustard or the HX salt of the Nitrogen Mustard is in a non-aqueous vehicle or carrier, wherein the non-aqueous vehicle or carrier does not include petrolatum or ethanol, wherein the Nitrogen Mustard is represented by the following structures:

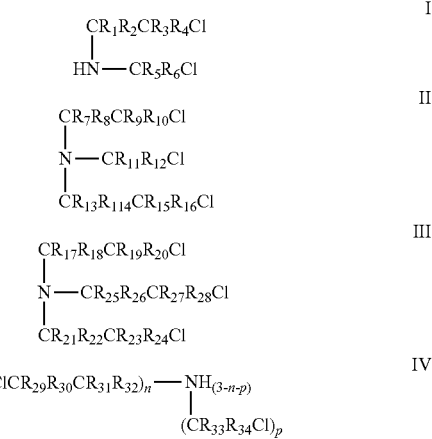

wherein each $R_1, R_2, R_3 \ldots R_{34}$ ($R_1$-$R_{34}$) is independently selected from the group consisting of a hydrogen atom, a linear alkyl group having 1-6 carbon atoms, a branched alkyl group having 2-12 carbon atoms, a cycloalkyl group having 3-17 carbon atoms, a fluorinated linear alkyl group having 2-12 carbon atoms, a fluorinated branched alkyl group having 2-12 carbon atoms, a fluorinated cycloalkyl group having 3-17 carbon atoms, an aryl group, an aralkyl group, an alkaryl group, a cycloalkyl group, a bicycloalkyl group, an alkenyl group, an alkalkenyl group, an alkenylalkyl group, an alkynyl group, an alkalkynyl group, an alkynylalkyl group, a trifluoropropyl group, a cyanopropyl group, an acryloyl group, an arylacryloyl group, an acryloylaryl group, an alkylacyl group, an arylacyl group, an alkylenylacyl group, and an alkynylacyl group, wherein n is 1, 2 or 3, wherein p is 0, 1 or 2, wherein n+p≦3, and wherein any two $R_1$-$R_{34}$ in the same molecule may be linked to form a three- to eight-membered cyclic group.

A second aspect of the present invention provides A method for treating a person with a skin disorder, comprising: topically applying to the affected skin a Nitrogen Mustard or an HX salt of the Nitrogen Mustard, wherein the Nitrogen Mustard or the HX salt of the Nitrogen Mustard is in a non-aqueous vehicle or carrier, wherein the non-aqueous vehicle or carrier does not include petrolatum or ethanol, wherein the Nitrogen Mustard is represented by the following structures:

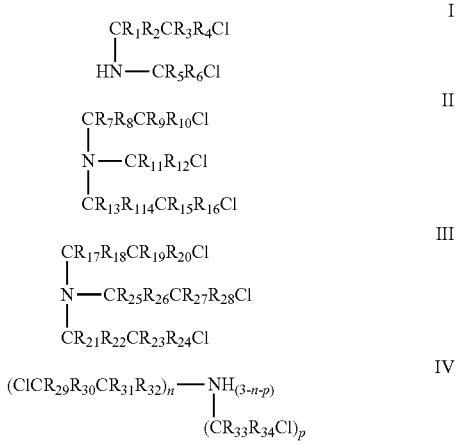

wherein each $R_1, R_2, R_3 \ldots R_{34}$ ($R_1$-$R_{34}$) is independently selected from the group consisting of a hydrogen atom, a linear alkyl group having 1-6 carbon atoms, a branched alkyl group having 2-12 carbon atoms, a cycloalkyl group having 3-17 carbon atoms, a fluorinated linear alkyl group having 2-12 carbon atoms, a fluorinated branched alkyl group having 2-12 carbon atoms, a fluorinated cycloalkyl group having 3-17 carbon atoms, an aryl group, an aralkyl group, an alkaryl group, a cycloalkyl group, a bicycloalkyl group, an alkenyl group, an alkalkenyl group, an alkenylalkyl group, an alkynyl group, an alkalkynyl group, an alkynylalkyl group, a trifluoropropyl group, a cyanopropyl group, an acryloyl group, an arylacryloyl group, an acryloylaryl group, an alkylacyl group, an arylacyl group, an alkylenylacyl group, and an alkynylacyl group, wherein n is 1, 2, or 3, wherein p is 0, 1 or 2, wherein n+p≦3, and wherein any two $R_1$-$R_{34}$ in the same molecule may be linked to form a three- to eight-membered cyclic group.

A third aspect of the present invention provides a method for stabilizing a volatile alkylating agent, comprising: providing a non-aqueous flowable ointment or cream, wherein the non-aqueous flowable ointment or cream does not include petrolatum or ethanol; reconstituting an HX salt of the volatile alkylating agent in anhydrous solvent; combining with mixing the non-aqueous flowable ointment or cream and the HX salt of the volatile alkylating agent.

A fourth aspect of the present invention provides an apparatus having a wall around a compartment, wherein the wall is made of a material that is impervious to a mixture of a pharmaceutically acceptable nitrogen mustard•HCl and a non-aqueous vehicle or carrier that does not include petrolatum or ethanol.

BRIEF DESCRIPTION OF THE DRAWINGS

The features of the invention are set forth in the appended claims. The invention itself, however, will be best understood by reference to the following detailed description of an illustrative embodiment when read in conjunction with the accompanying drawings, wherein:

DETAILED DESCRIPTION OF THE INVENTION

Figure 1:
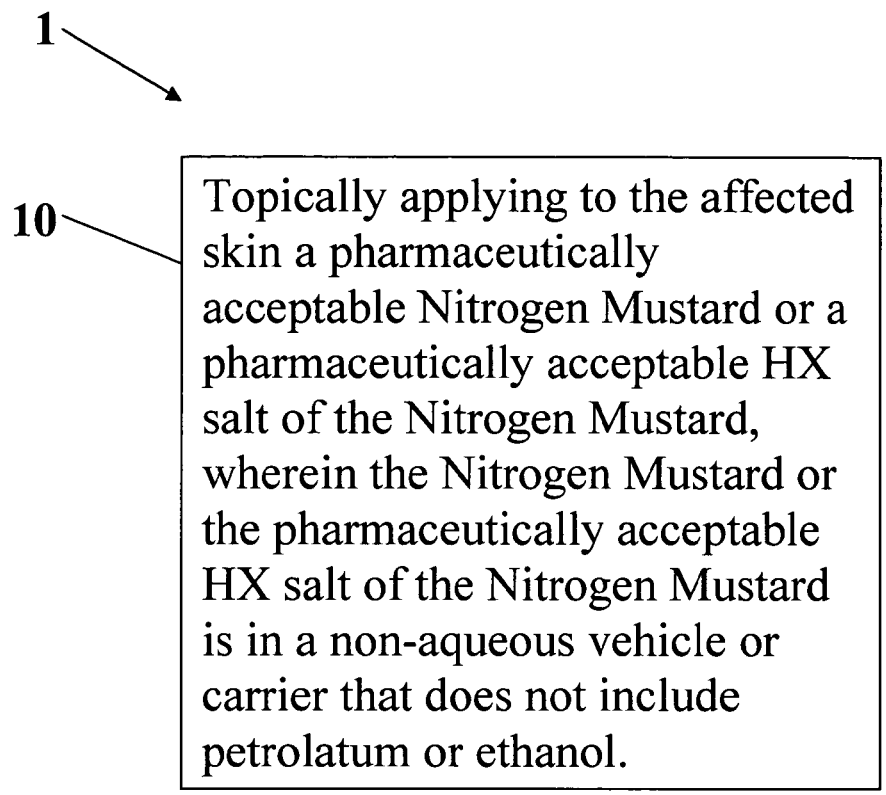
FIG. 1 illustrates a method for the use of compositions having stabilized alkylating agents for treating skin disease, in accordance with embodiments of the present invention.

In an embodiment, patients having MF topically treated with Nitrogen Mustard compounded into a polypropylene glycol (PPG, molecular weight from about 300 to about 2500), propylene glycol (PG,), polyethyleneglycol (PEG, molecular weight from about 100 to about 1000) or ethylene glycol ointment or cream showed no evidence of any systemic toxicities.

Table 1 below provides a summary of topical treatment of patients having MF with nitrogen mustard in propylene glycol (PG), including response rates and toxicities.

TABLE 1

Topical Nitrogen Mustard In Mycosis Fungoides (MF): Summary Of Clinical Outcomes & Toxicities.

| #PTS | F/U (YRS) | VEHICLE | DOSE | % CR | % PCR | % HYPERSENSITIVITY REACTIONS | % SYSTEMIC TOXICITIES* |
|---|---|---|---|---|---|---|---|
| 14 | <1 | PG | 10 mg % Topically Applied Once Daily | 36% | 42% | 7% | 0% |

*Systemic toxicities monitored by serial History & Physicals and laboratory studies.
Abbreviations: PTS = patients studies; F/U = follow-up; CR = complete response; PG = propylene glycol, PCR = partial response; NR = not reported Systemic Absorption There is no evidence of any clinically significant systemic absorption of topically applied Nitrogen Mustard. No systemic toxicities from percutaneous absorption have been observed in long-term topical Nitrogen Mustard use in MF.

Genetic toxicity—No genetic toxicity has been observed with the use of topical Nitrogen Mustard application. This is best documented in a study that demonstrated no effect on sister-chromatid exchanges in the peripheral blood lymphocytes of CTCL-MF patients assayed before and after topical Nitrogen Mustard treatment.

Bone Marrow Suppression—No evidence of bone marrow suppression (anemia, leukoopenia or thrombocytopenia) has reported with long term use of topical Nitrogen Mustard, based on serial monitoring of the complete blood count.

Hepatotoxicity—No evidence of hepatotoxicity has reported with long term use of topical NM, based on serial monitoring of peripheral blood liver function tests.

Nephrotoxicity—No evidence of nephrotoxicity has reported with long term use of topical Nitrogen Mustard, based on serial monitoring of peripheral blood renal function tests.

Environmental Contamination

Minimal evidence of environmental contamination has also been demonstrated with topical Nitrogen Mustard use.

Cutaneous Side Effects

Hyperpigmentation—resulting from the direct melanogenic effects of Nitrogen Mustard, has been reported in a large percentage of treated patients. The hyperpigmentation is reversible and decreases gradually in most patients even if topical therapy is continued.

Contact dermatitis—is a common complication of topical Nitrogen Mustard application. An irritant contact dermatitis is most common and can be seen in up to 25% of individuals using topical Nitrogen Mustard ointment, particularly if used in sensitive areas such as the face or skin folds. Allergic contact dermatitis is also observed with topical Nitrogen Mustard use.

Immediate-type (urticarial) reactions—are rare.

Allergic contact dermatitis—from delayed-type hypersensitivity (DTH) reactions is more common and appears to be dose dependent. Higher concentrations of aqueous preparations are associated with a DTH frequency of 10-67%. Desensitization with lower concentrations of Nitrogen Mustard has been successfully employed in patients with DTH reactions to Nitrogen Mustard. The use of a lower concentration ointment preparation dramatically reduces the incidence DTH reactions. Stanford University reported 0% DTH reactions in patients using Nitrogen Mustard ointment for the first time and an 8% frequency of DTH in patients with a previous history of HN hypersensitivity, in their series utilizing an Nitrogen Mustard ointment preparation.

Pediatric Use

Topical Nitrogen Mustard has been reported to be used in children and adolescences (<18 years) without any significant differences in toxicities than in adults.

Use in Pregnancy

Despite the lack of evidence of percutaneous absorption of topical Nitrogen Mustard, the use of topical Nitrogen Mustard has historically been avoided in pregnant and nursing women.

Cutaneous Carcinogenesis

There are no reports of a significantly increased incidence of squamous cell carcinoma (SCC) of the skin with prolonged use of topical Nitrogen Mustard. Several groups have reported an approximately 10% (4%-14%) frequency of SCC in CTCL-MF patients using topical Nitrogen Mustard and suggest a potential risk of epidermal carcinogenesis. These retrospective studies, however, do not account for confounding variables, such as CTCL-MF associated risk for second malignancies, prior therapies (e.g. radiation therapy to the skin), and do not have adequate control groups.

In normal DNA strand replication, a DNA strand having deoxyribonucleosides, wherein each deoxyribonucleoside may include a base adenine (A), thymine (T), cytosine (C) and guanine (G), replicates by linking each deoxyribonucleoside on the strand with another deoxyribonucleoside, wherein typical linking occurs between adenine (A) and thymine (T), forming an A-T linkage and between cytosine (C) and guanine (G), forming a C-G linkage between the original DNA strand and its replicated DNA strand.

Nitrogen Mustard alkylating agents may act as anti-cancer agents by impairing natural DNA strand replication of cancer cells, allowing unnatural base-base linkages such as a guanine (G) base linking to another guanine (G) base if the particular Nitrogen Mustard alkylating agents are bifunctional alkylators. Hereinafter, bifunctional alkylators are Nitrogen Mustards having at least two 2-chloroethyl side chains, e.g. bis-(2-chloroethyl)methyl amine, such as structure I of Reaction 1, infra.

Reaction 1, infra, depicts a reversible reaction, represented by forward reaction 1a and reverse reaction 1b in Reaction 1, in which a Nitrogen Mustard alkylating agent having a 2-chloroethyl side chain, e.g., bis-(2-chloroethyl)methylamine, represented by structure I, infra, may undergo an intramolecular cyclization, resulting in formation of a highly reactive ethyleniminium intermediate (aziridinium cation), represented by a structure II, infra. A concentration of the aziridinium cation, II, infra, may be in equilibrium with a concentration of the Nitrogen Mustard, I, infra, wherein the equilibrium constant $K_{eq(1a,1b)}$ may be represented by a ratio of a rate $k_{1a}$, of the forward reaction 1a, to a rate $k_{1b}$, of the reverse reaction 1b.

Reaction 1: Formation of Aziridinium Cation, Represented by Structure II, infra.

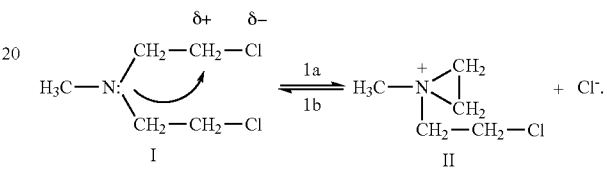

In structure I, a carbon atom bonded to chlorine may initially have a partial positive charge, $\delta+$, and a chlorine atom may initially have a partial negative charge, $\delta-$. In Reaction I, an unshared pair of electrons of nitrogen may form a covalent bond to the carbon having $\delta+$, releasing the chlorine atom as chloride, and forming structure II.

Structure II, supra, may undergo nucleophilic attack by an electron donor, i.e., a nucleophile, resulting in alkylating the nucleophile. Reaction with the nucleophile guanine (G), structure III, shown in Reaction 2, supra, at position N-7 of the guanine (G) occurs to the greatest extent. Other sites on guanine (G), and other DNA bases such as adenine (A), cytosine (C) and thymine (T), and phosphate oxygens also can be alkylated. Hereinafter, structure III represents all stereoisomers and racemates of the deoxyribonucleoside having any DNA base.

Reaction 2: Nucleophilic attack by guanine on the unstable aziridinium ring, structure II, resulting from the intramolecular cyclization shown in Reaction 1, supra.

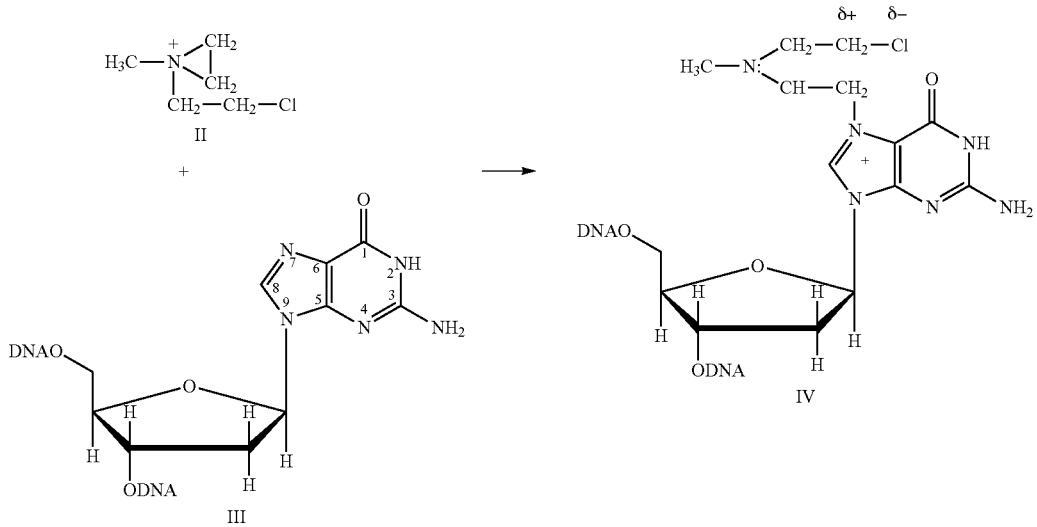

Reaction 2, supra, results in forming the alkylated deoxyribonucleoside, structure IV. In Reaction 2 supra, position N-7 of the guanine (G) base of the deoxyribonucleoside, represented in structure III, may nucleophilically attack the aziridinium ring, structure II, that may have been formed by the intramolecular cyclization represented by Reaction 1, supra, resulting in alkylating position N-7 of the guanine (G) base of structure III. Hereinafter, structure IV represents all stereoisomers and racemates of the deoxyribonucleoside having any DNA base.

Alkylating agents have four actions on nucleic acids. First of all, the agent may cause crosslinking of DNA strands which interferes with DNA and RNA synthesis. This is thought to be the most important reason for the cytotoxic effect of alkylating agents. Secondly, the agent may alter the "side chain groups" of the nucleotide base ring which would lead to abnormal base pairing and point mutations in the synthesized DNA and RNA chains. Thirdly, the alkylating agent may split the base ring from the nucleotide which again interrupts proper DNA and RNA synthesis. Finally, the alkylating agent may break the ring structure of a nucleotide base which would prevent base pairing during DNA and RNA synthesis.

In normal DNA strand replication, a DNA strand consisting of deoxyribonucleosides, wherein each deoxyribonucleoside may include a base adenine (A), thymine (T), cytosine (C) and guanine (G), replicates by linking each deoxyribonucleoside on the strand with another deoxyribonucleoside, wherein typical linking occurs between adenine (A) and thymine (T), forming an A-T linkage and between cytosine (C) and guanine (G), forming a C-G linkage between the original DNA strand and its replicated DNA strand.

Nitrogen Mustard alkylating agents may act as anti-cancer agents by impairing normal DNA strand replication, allowing abnormal base-base linkages such as a guanine (G) base linking to another guanine (G) base if the particular Nitrogen Mustard alkylating agents are bifunctional alkylators. Hereinafter, bifunctional alkylators are Nitrogen Mustards having at least two 2-chloroethyl side chains, e.g. bis-(2-chloroethyl) methyl amine, structure I, supra.

In Reaction 2, supra, one of the 2-chloroethyl side chains of the deoxyribonucleoside represented by the structure IV has alkylated the guanine (G) base of the structure III. In reversible Reaction 3, infra, the remaining 2-chloroethyl side chain of the deoxyribonucleoside of the structure IV has also undergone an intramolecular cyclization, resulting in formation of deoxyribonucleoside V, having the highly reactive aziridinium ring.

Reaction 3: Formation of Aziridinium Cation from the remaining 2-chloroethyl side chain of the deoxyribonucleoside of the structure IV, supra.

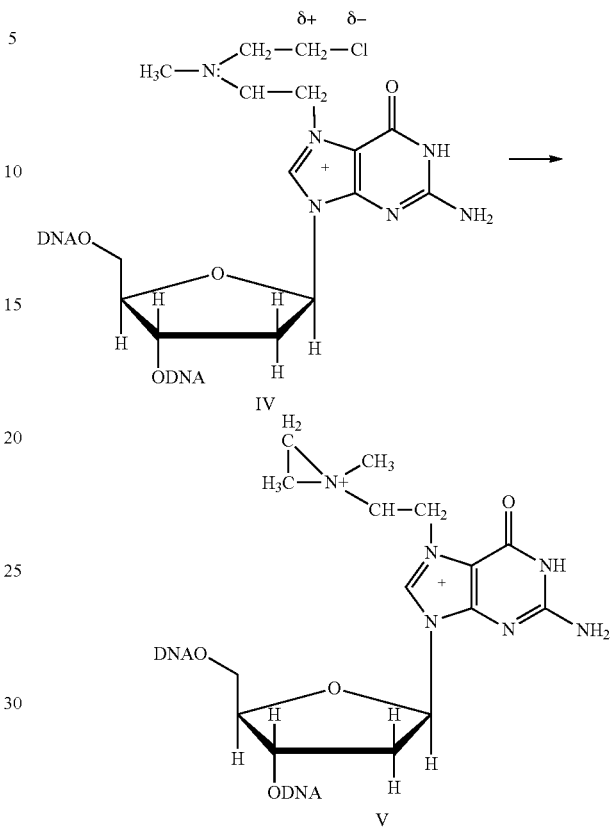

Reaction 4, infra, depicts the abnormal linking of the deoxyribonucleoside V, having a guanine (G) base and the activated aziridinium ring, with another deoxyribonucleoside III, also having a guanine (G) base, forming an abnormal guanine-guanine (G-G) link in the product, represented by the structure VI. Hereinafter, structure VI represents all stereoisomers and racemates of the product from coupling two molecules of the deoxyribonucleoside represented by structure III at the N-7 position with the bifunctional alkylating Nitrogen Mustard represented by the structure II, supra.

Reaction 4: The Abnormal Linking of the Deoxyribonucleoside V, Having a Guanine (G) Base and the Activated Aziridinium Ring, With Another Deoxyribonucleoside, VI, Also Having a Guanine (G) Base.

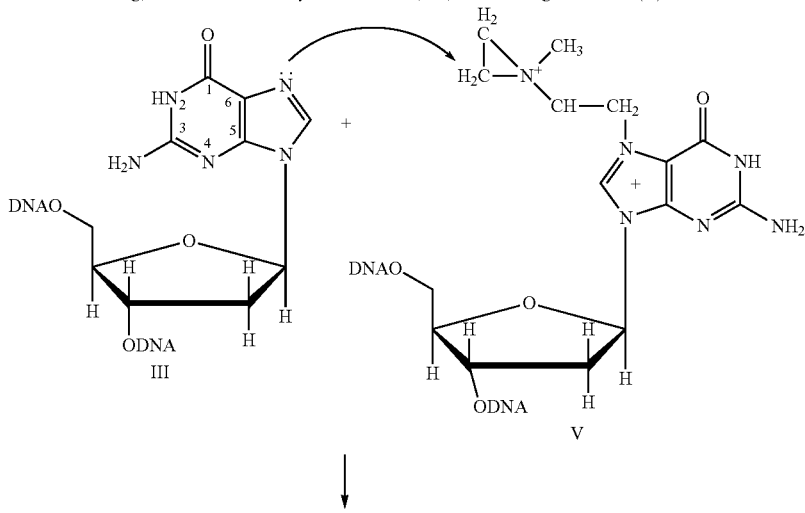

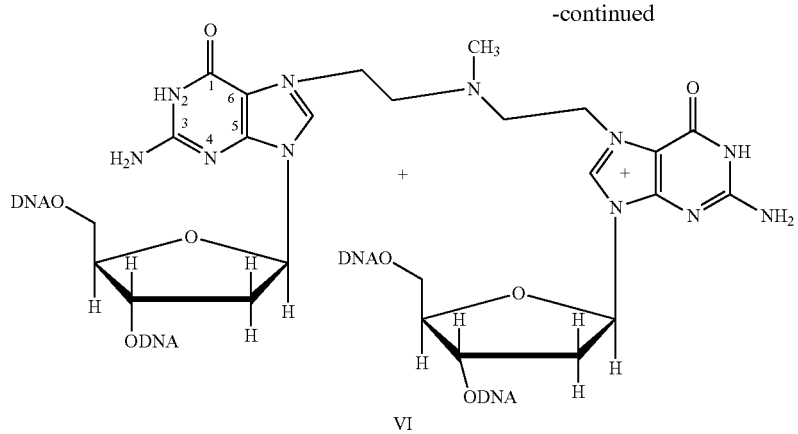

VI

A highly unstable nature and extremely short duration of action of the Nitrogen Mustards in the presence of water may result because water may decompose the highly reactive ethyleniminium intermediate (aziridinium cation), represented by the structure II, in Reaction 1, supra, replacing the chlorine atom on the 2-chloroethyl side chains of the Nitrogen Mustard by an OH group. The Nitrogen Mustards are said to be highly unstable and have an extremely short duration of action because they may react with water, resulting in replacement of one or both of the chlorine atoms by a hydroxyl (OH) group. Replacement of the chlorine atoms may block formation of the aziridinium cation and therefore may prevent the Nitrogen Mustards from acting as alkylating agents of, for example, the N-2 position of the guanine base of DNA. Reaction 5 illustrates competing equilibrium reactions, 1a and 1b and 5a and 5b. In Reactions 1a and 1b, a free form of the Nitrogen Mustard, structure I, may be in equilibrium with the aziridinium ion II, as described for Reaction 1, supra. The equilibrium constant for Reactions 1a and 1b has been described as $K_{eq(1a,1b)}$, supra. In like manner, the equilibrium constant for Reactions 5a and 5b, $K_{eq(5a,5b)}$ may be expressed as the ratio of the concentration of the HX salt, IX, to the product of the concentration of the free form of the Nitrogen Mustard, structure I and the concentration of HX. Therefore, in an embodiment, there may be an equilibrium concentration of aziridinium cation represented by the ratio of $K_{eq(1a,1b)}$ to $K_{eq(5a,5b)}$, even when the Nitrogen Mustard has been stabilized by converting the free base form of the Nitrogen Mustard, as represented by structure I, infra, as illustrated by Reaction 5, infra, to its HX salt, as represented by the structure IX. Therefore, the N-2 position of the guanine base of DNA, structure III in Reactions 2-4 may be alkylated by the HX salt IX, as in Reaction 5, infra, because the concentration of the aziridinium cation in Reaction 5, infra, may be a real positive number, equal to $K_{eq(1a,1b)}$ to $K_{eq(5a,5b)}$. Hereinafter, the free base form of the Nitrogen Mustard is any non-salt form of the Nitrogen Mustard, wherein a lone pair of electrons on the nitrogen atom may be available for forming the aziridinium ion, II, as in Reaction 1, supra. In embodiments of the present invention, the aziridinium cation, Structure II, supra, may undergo nucleophilic attack by an electron donor, resulting in alkylating the nucleophile. For example, reaction with the nucleophile guanine (G), structure III, shown in Reaction 2, supra, at position N-7 of the guanine (G) occurs to the greatest extent. Other sites on guanine (G), and other DNA bases such as adenine (A), cytosine (C) and thymine (T), and phosphate oxygens also can be alkylated.

The inventors disclose that oxygen of primary alcohols often are nucleophiles and therefore may have a disadvantageous effect on the use of the free base or the pharmaceutically acceptable HX salt IX, as in reaction 5, infra, because the free base of the nitrogen mustard or the pharmaceutically acceptable HX salt IX is consumed in the undesirable side reaction in which the nucleophile is alkylated by the free base of the nitrogen mustard or the pharmaceutically acceptable HX salt IX, instead of being available to act as an anti-cancer agent against T-Cell lymphoma, for example, by impairing normal DNA strand replication. Hereinafter, pharmaceutically acceptable HX salt IX, as in reaction 5, infra, refers to salt forms that are pharmacologically acceptable and substantially non-toxic to the subject being treated with the compound of the invention. Therefore, secondary and tertiary alcohols, amines, amino alcohols having from 1 to 20 carbon atoms are preferred over primary alcohols having from 1 to 20 carbon atoms in formulations of the free base of the nitrogen mustard or the pharmaceutically acceptable HX salt IX, when a pharmaceutically acceptable inert ingredient, i.e., a pharmaceutically acceptable excipient, may be needed to promote solubilization of the free base of the nitrogen mustard or the pharmaceutically acceptable HX salt IX in the non-aqueous vehicle or carrier that does not include petrolatum or ethanol.

Ethyl alcohol is not used to dissolve the nitrogen mustard or its HX salt because it is a nucleophile that degrades the nitrogen mustard or its HX salt by promoting loss of chlorine. Isopropyl, cetyl, stearyl, cetearyl, or lanolin alcohol are preferred pharmaceutically acceptable excipients for dissolving or taking up the nitrogen mustard or its HX salt. Alternatively, for example, for topical formulations, pharmaceutically acceptable excipients may comprise solvents, emollients, humectants, preservatives, emulsifiers, and pH agents. Suitable solvents include acetone, glycols, polyurethanes, and others known in the art. Suitable emollients include mineral oil, propylene glycol dicaprylate, lower fatty acid esters, lower alkyl ethers of propylene glycol, cetyl alcohol, cetostearyl alcohol, stearyl alcohol, stearic acid, wax, and others known in the art. Suitable humectants include glycerin, sorbitol, and others known in the art. Suitable emulsifiers include glyceryl monostearate, glyceryl monoleate, stearic acid, polyoxyethylene cetyl ether, polyoxyethylene cetostearyl ether, polyoxyethylene stearyl ether, polyethylene glycol stearate, propylene glycol stearate, and others known in the art. Suitable pH agents include hydrochloric acid, phosphoric acid, diethanolamine, triethanolamine, sodium hydroxide, monobasic sodium phosphate, dibasic sodium phosphate, and others known in the art. Alternatively, pH agents include from about 1 percent by weight to about 15 percent by weight acetic acid, citric acid or lactic acid. Suitable preservatives include benzyl alcohol, sodium benzoate, parabens, and others known in the art.

The inventors disclose that polyethylene glycol (PEG), ethylene glycol (EG), polypropylene glycol (PPG), propylene glycol (PG) and the diethylene glycol monosubstituted ether (DGMSE) are useful pharmaceutically acceptable excipients. The polyethylene glycol (PEG), ethylene glycol (EG), polypropylene glycol (PPG), propylene glycol (PG) and the diethylene glycol monosubstituted ether (DGMSE) that may hydrogen bond to trace nucleophiles that may be contaminants in the pharmaceutically acceptable excipients, thereby reducing the nucleophilic strength of the trace nucleophiles. Therefore diethylene glycol monosubstituted ether (DGMSE) or silicones such as dimethicone or cyclomethicone are useful as pharmaceutically acceptable excipients to promote dissolution of the free base of the nitrogen mustard or the HX salt IX, infra, in formulations of the free base of the nitrogen mustard or the pharmaceutically acceptable HX salt IX, infra.

In embodiments of the present invention, pharmaceutically acceptable HX salts of the Nitrogen Mustard, structure IX, infra, are more stable and of longer activity duration than their respective free bases, as measured by an effective alkylating activity of the pharmaceutically acceptable HX salts of the Nitrogen Mustard, structure IX, infra, in the non-aqueous vehicle or carrier that does not include petrolatum or ethanol, wherein an effective alkylating activity of the pharmaceutically acceptable HX salts in the non-aqueous vehicle or carrier that does not include petrolatum or ethanol after three (3) years is equivalent to the effective alkylating activity of the free base form of the respective Nitrogen Mustards, structure I, after 3 months in the non-aqueous vehicle or carrier that does not include petrolatum or ethanol. The non-aqueous vehicle or carrier that does not include petrolatum or ethanol in formulations of the nitrogen mustard free base or the pharmaceutically acceptable HX salts, structure IX, infra, does not include any grade of white or yellow petrolatum recognized in the art as suitable for human application. The non-aqueous vehicle or carrier that does not include petrolatum or ethanol does not include material commercially available as Penreco Snow White Pet USP in formulations of the nitrogen mustard free base or the pharmaceutically acceptable HX salts, structure IX, infra. The non-aqueous vehicle or carrier that does not include petrolatum or ethanol does not include hydrocarbon mixtures formulated with mineral oils in combination with paraffin waxes of various melting points in formulations of the nitrogen mustard free base or the pharmaceutically acceptable HX salts, structure IX, infra. The non-aqueous vehicle or carrier that does not include petrolatum or ethanol does not include lipophilic emollient selected from the group consisting of: petrolatum; esters of fatty acids. Hereinafter, the effective alkylating activity of the pharmaceutically acceptable HX salts, structure IX, infra, in the non-aqueous vehicle or carrier that does not include petrolatum or ethanol is equivalent to the effective alkylating activity of the free base form of the respective Nitrogen Mustards in the non-aqueous vehicle or carrier that does not include petrolatum or ethanol when a weight percent of the pharmaceutically acceptable HX salt, structure IX, infra, in the non-aqueous vehicle or carrier that does not include petrolatum or ethanol is essentially equal to the weight percent of the respective free base of the Nitrogen Mustard, structure I in the non-aqueous vehicle or carrier that does not include petrolatum or ethanol.

In embodiments of the present invention, use of the pharmaceutically acceptable HX salt, structure IX, infra, of the Nitrogen Mustard in the non-aqueous vehicle or carrier that does not include petrolatum or ethanol may preserve the effective alkylating activity by reducing its volatility compared to that of the free base form, since pharmaceutically acceptable HX salts of Nitrogen Mustards generally have lower vapor pressures than their corresponding free base forms.

Reaction represented by arrow 5c, infra, illustrates formation of the stabilized Nitrogen Mustard•HX compositions of the present invention that have been stabilized by converting said free form highly reactive Nitrogen Mustard alkylating agents to pharmaceutically acceptable HX salts by reaction of the Nitrogen Mustard with HX.

Reaction 5: Formation of Nitrogen Mustard•HX, Represented by Structure IX, wherein the Nitrogen Mustard is Represented by Structure I, as in Reaction 1, supra.

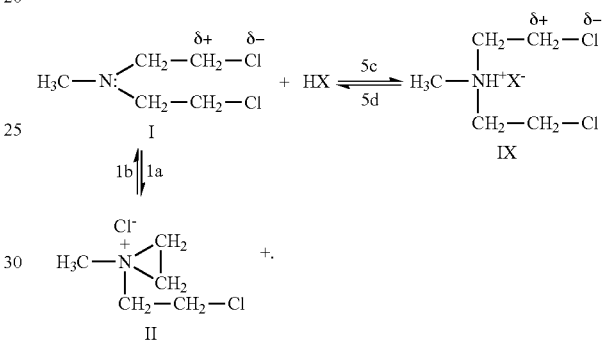

In an embodiment, $X^-$ may advantageously be halide, such as $Cl^-$, $Br^-$, $I^-$ or $HSO_4^-$ or $NO_3$, wherein HX may be respectively, HCl, HBr, HI, or $H_2SO_4$, or $HNO_3$. Alternatively pharmaceutically acceptable HX salts include conventional acid-addition salts or base-addition salts formed from suitable non-toxic organic or inorganic acids or inorganic bases. Exemplary acid-addition salts include those derived from inorganic acids such as hydrochloric acid, hydrobromic acid, hydroiodic acid, sulfuric acid, sulfamic acid, phosphoric acid, and nitric acid, and those derived from organic acids such as p-toluenesulfonic acid, methanesulfonic acid, ethane-disulfonic acid, isethionic acid, oxalic acid, p-bromophenylsulfonic acid, carbonic acid, succinic acid, citric acid, benzoic acid, 2-acetoxybenzoic acid, acetic acid, phenylacetic acid, propionic acid, glycolic acid, stearic acid, lactic acid, malic acid, tartaric acid, ascorbic acid, maleic acid, hydroxymaleic acid, glutamic acid, salicylic acid, sulfanilic acid, and fumaric acid. Exemplary base-addition salts include those derived from ammonium hydroxides (e.g., a quaternary ammonium hydroxide such as tetramethylammonium hydroxide), those derived from inorganic bases such as alkali or alkaline earth-metal (e.g., sodium, potassium, lithium, calcium, or magnesium) hydroxides, and those derived from non-toxic organic bases such as basic amino acids.

Hereinafter, the pharmaceutically acceptable Nitrogen Mustard or the pharmaceutically acceptable HX salt of the Nitrogen Mustard is an active pharmaceutical ingredient (API). In an embodiment, the API may be provided as a 10:1 weight ratio of NaCl:API. Alternatively the weight ratio of NaCl to the API may be from about 100:0.01 to 0.01:100. Alternatively the API may be formulated into any solid mixture having one or more of the above mentioned pharmaceutically acceptable HX salts. The inventors disclose that in theory the API, as the HX salt is stabilized in a salt matrix because the salt matrix and the HX salt of the API are both ionic.

FIG. 1 depicts an embodiment of the present invention, a method 1, for treating a person with a skin disorder, comprising: a step 10, topically applying to the affected skin a pharmaceutically acceptable Nitrogen Mustard or a pharmaceutically acceptable HX salt of the Nitrogen Mustard, wherein the Nitrogen Mustard or the pharmaceutically acceptable HX salt of the Nitrogen Mustard is in a non-aqueous vehicle or carrier that does not include petrolatum or ethanol, wherein the Nitrogen Mustard is represented by the following structures:

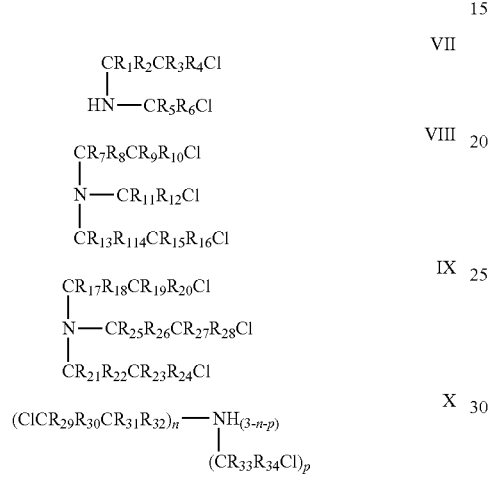

In an embodiment, each $R_1$, $R_2$, $R_3$ ... $R_{34}$ ($R_1$-$R_{34}$) is independently selected from the group consisting of a hydrogen atom, a linear alkyl group having 1-6 carbon atoms, a branched alkyl group having 2-12 carbon atoms, a cycloalkyl group having 3-17 carbon atoms, a fluorinated linear alkyl group having 2-12 carbon atoms, a fluorinated branched alkyl group having 2-12 carbon atoms, a fluorinated cycloalkyl group having 3-17 carbon atoms, an aryl group, an aralkyl group, an alkaryl group, a cycloalkyl group, a bicycloalkyl group, an alkenyl group, an alkalkenyl group, an alkenylalkyl group, an alkynyl group, an alkalkynyl group, an alkynylalkyl group, a trifluoropropyl group, a cyanopropyl group, an acryloyl group, an arylacryloyl group, an acryloylaryl group, an alkylacyl group, an arylacyl group, an alkylenylacyl group, and an alkynylacyl group.

In an embodiment, n is 1, 2, or 3.

In an embodiment, p is 0, 1, or 2 and n+p≦3.

In an embodiment, any two $R_1$-$R_{34}$ in the same molecule may be linked to form a three- to eight-membered cyclic group.

In an embodiment, the Nitrogen Mustard is advantageously selected from the group consisting of bis-(2-chloroethyl)ethylamine, bis-(2-chloroethyl)methylamine, and tris-(2-chloroethyl)amine, and combinations thereof. Hereinafter, structures VII, VIII, IX and X (XI-XIV) may represent all racemic forms and stereoisomers wherein said compounds may be capable of optical activity.

Alternatively, in an embodiment, the Nitrogen Mustard may be advantageously derived from a Nitrogen Mustard prodrug represented by the following structures:

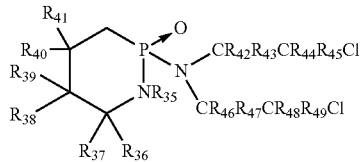

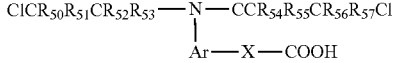

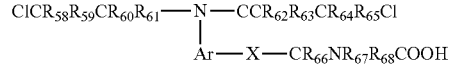

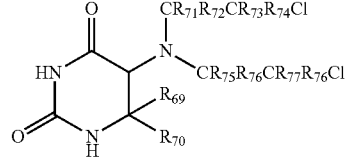

In an embodiment, each $R_{35}$, $R_{36}$, $R_{37}$ ... $R_{78}$ ($R_{35}$-$R_{78}$) is independently selected from the group consisting of a hydrogen atom, a linear alkyl group having 1-6 carbon atoms, a branched alkyl group having 2-12 carbon atoms, a cycloalkyl group having 3-17 carbon atoms, a fluorinated linear alkyl group having 2-12 carbon atoms, a fluorinated branched alkyl group having 2-12 carbon atoms, a fluorinated cycloalkyl group having 3-17 carbon atoms, an aryl group, an aralkyl group, an alkaryl group, a cycloalkyl group, a bicycloalkyl group, an alkenyl group, an alkalkenyl group, an alkenylalkyl group, an alkynyl group, an alkalkynyl group, an alkynylalkyl group, a trifluoropropyl group, a cyanopropyl group, an acryloyl group, an arylacryloyl group, an acryloylaryl group, an alkylacyl group, an arylacyl group, an alkylenylacyl group, and an alkynylacyl group.

In an embodiment, any two $R_1$-$R_{57}$ in the same molecule may be linked to form a three- to eight-membered cyclic group.

In an embodiment, each X group is a linking group selected from the group consisting of a linear or branched alkylene having 1 to 7 carbon atoms, a cycloalkylene having 3 to 17 carbon atoms, an alkylcycloalkylene having 4 to 20 carbon atoms, a cycloalkylalkylene having 4 to 20 carbon atoms, an arylene, having 4 to 30 carbon atoms, an alkylarylene, having 4 to 30 carbon atoms, an arylalkylene, having 4 to 30 carbon atoms, and combinations thereof, In an embodiment, each Ar group is a bifunctional aromatic linking group, wherein each Ar is selected from the group consisting of an arylene group, a substituted arylene group and/or a heteroarylene group.

Compounds represented by structures XI, XII, . . . XIV (XI-XIV) may be prodrug candidate forms of the Nitrogen Mustards, because they can be metabolized in vivo to generate the active Nitrogen Mustard. Hereinafter, a "prodrug" is a precursor (forerunner) of the active Nitrogen Mustard. A prodrug may undergo chemical conversion by metabolic processes to the parent drug, thus becoming an active Nitrogen Mustard. Hereinafter, structures XI, XII, . . . XIV (XI-XIV) may represent all racemic forms and stereoisomers, wherein said compounds may be capable of optical activity.

For example, phosphatase and phosphamidase enzymes may hydrolyze the P—N bond of structure XI, supra, e.g., cyclophosphamide, structure XIA, infra or ifosphamide, structure XIB, infra, resulting in an intermediate aldophosphamide, which may nonenzymatically break down to a bifunctional phosphoramide mustard. In an embodiment, cyclophosphamide, structure XIA, supra or ifosphamide, structure XIB, supra may be oxidatively activated by cytochrome P-450

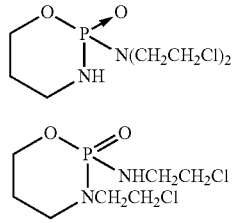

In an embodiment, structure XII, supra, e.g., Chlorambucil, structure XIIA, infra, may be a bifunctional alkylating agent of the nitrogen mustard type.

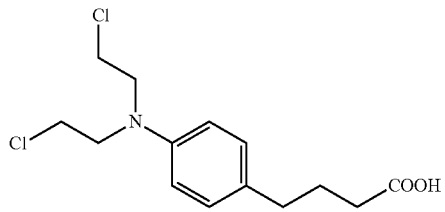

Structure XII may be cell cycle-phase nonspecific, although it also may be cytotoxic to nonproliferating cells. Activity may occur as a result of formation of an unstable ethylenimmonium ion, which alkylates or binds with many intracellular molecular structures, including nucleic acids. Its cytotoxic action may be primarily due to cross-linking of strands of DNA, which inhibits nucleic acid synthesis.

In an embodiment structure, XIII, supra, e.g., 4-Bis(2-chloroethyl)amino-L-phenylalanine, Melphalan, structure XIIIA, infra, may be a bifunctional alkylating agent of the nitrogen mustard type.

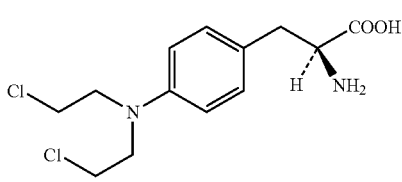

Like the nitrogen mustard prodrugs of structure XII, prodrugs of structure XIII may be cell cycle-phase nonspecific, although they also may be cytotoxic to nonproliferating cells.

In an embodiment, structure XIV, supra, e.g., uracil mustard, structure XIVA, infra, may be a bifunctional alkylating agent of the nitrogen mustard type.

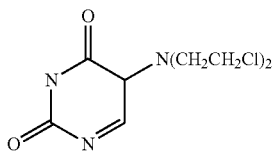

In an embodiment, the pharmaceutically acceptable HX salt of the Nitrogen Mustard may be advantageously selected from the group consisting of Nitrogen Mustard•HCl, Nitrogen Mustard•$H_2SO_4$, Nitrogen Mustard•$HNO_3$, Nitrogen Mustard •$H_2SO_4$, Nitrogen Mustard•HBr, Nitrogen Mustard•HI and combinations thereof.

In an embodiment, an ingredient of the non-aqueous vehicle or carrier that does not include petrolatum or ethanol may be polyethylene glycol (PEG) or ethylene glycol (EG), polypropylene glycol (PPG) or propylene glycol (PG), diethylene glycol monosubstituted ether (DGMSE), $HOCH_2CH_2OCH_2CH_2OR_{79}(HO(CH_2CH_2O)_2R_{79})$, wherein $R_{79}$ is selected from the group consisting of a linear alkyl group having 1-6 carbon atoms, a branched alkyl group having 2-12 carbon atoms, a cycloalkyl group having 3-17 carbon atoms, a fluorinated linear alkyl group having 2-12 carbon atoms, a fluorinated branched alkyl group having 2-12 carbon atoms, a fluorinated cycloalkyl group having 3-17 carbon atoms, an aryl group, an aralkyl group, an alkaryl group, a cycloalkyl group, a bicycloalkyl group, an alkenyl group, an alkalkenyl group, an alkenylalkyl group, an alkynyl group, an alkalkynyl group, an alkynylalkyl group, a trifluoropropyl group, a cyanopropyl group, an acryloyl group, an arylacryloyl group, an acryloylaryl group, an alkylacyl group, an arylacyl group, an alkylenylacyl group and an alkynylacyl group.

In an embodiment, each ingredient of the non-aqueous vehicle or carrier that does not include petrolatum or ethanol may be selected from the group consisting of Ethoxy Diglycol Reagent, Hydroxypropylcellulose, buffer gel, Menthol Crystals USP, Butylated Hydroxytoluene NF, Glycerin USP, Edetate Disodium USP, Decyl Methyl Sulfoxide, Kris-Ester 236 and combinations thereof.

Buffer gel is selected from the group consisting of 2-Propenoic acid, Acrylate, Acrylic acid, Propenoate, Vinylformic acid, Acroleic acid, Ethylenecarboxylic acid, Propenoic acid, CH2=CHCOOH, Propene acid, Kyselina akrylova, Glacial acrylic acid, Ethylenecarboxylic acid, Acide acrylique [French], Acido acrilio [Spanish], Glacial acrylic acid, Kyselina akrylova [Czech], Propene acid, 2-Propenoic acid, homopolymer, Acrylic acid homopolymer, Acrylic acid polymer, Acrylic acid resin, Acrylic polymer, Acrylic polymer resins, Acrylic resin, Acrysol A 1, Acrysol A 3, Acrysol A 5, Acrysol AC 5, Acrysol WS-24, Acrysol ase-75, Acrysol lmw-20X, Antiprex 461, Antiprex A, Arasorb 750, Arasorb S 100F, Arolon, Aron, Aron A 10H, Atactic poly(acrylic acid), CCRIS 3234, Carbomer, Carbomer 1342, Carbomer 910, Carbomer 910 [USAN], Carbomer 934 [USAN], Carbomer 934p [USAN], Carbomer 940 [USAN], Carbomer 941 [USAN], Carbopol 1342, Carbopol 910, Carbopol 934, Carbopol 934P, Carbopol 940, Carbopol 941, Carbopol 960, Carbopol 961, Carbopol 971P, Carbopol 974P, Carbopol 980, Carbopol 981, Carboset 515, Carboset Resin No. 515, Carboxy vinyl polymer, Carboxypolymethylene, Carpolene, Colloids 119/50, Cyguard 266, Dispex C40, Dow Latex 354, G-Cure, Good-rite K 37, Good-rite K 702, Good-rite K 732, Good-rite K-700, Good-rite K727, Good-rite WS 801, Haloflex 202, Haloflex 208, Joncryl 678, Junlon 110, Jurimer AC 10H, Jurimer AC 10P, NSC 106034, NSC 106035, NSC 106036, NSC 106037, NSC 112122, NSC 112123, NSC 114472, NSC 165257, Nalfloc 636, Neocryl A-1038, OLD 01, P 11H, P-11H, PA 11M, PAA-25, POLYACRYLIC ACID, Pemulen TR-1, Pemulen TR-2, Poly(acrylic acid), Polyacrylate, Polyacrylate elastomers, Polymer of 2-propenoic acid, cross-linked with allyl ethers of pentaerythritol, Polymer of 2-propenoic acid, cross-linked with allyl ethers of sucrose, Polymer of 2-propenoic acid, cross-linked with allyl ethers of sucrose or pentaerythritol, Polymer of acrylic acid, cross-linked with allyl ethers of pentaerythritol, Polymer of acrylic acid, cross-linked with allyl ethers of sucrose or pentaerythritol, Polymer, carboxy vinyl, Polymerized acrylic acid, Polytex 973, Primal ASE 60, Propenoic acid polymer, R968, Racryl, Revacryl A 191; Rohagit SD 15, Sokalan PAS, Solidokoll N, Synthemul 90-588, TB 1131, Tecpol, Texcryl, Versicol E 7, Versicol E15, Versicol E9, Versicol K 11, Versicol S 25, Viscalex HV 30, Viscon 103, WS 24, WS 801, XPA, 54182-57-9, 9007-20-9, CARBOMER, Carbomere [INN-French], Carbomero [INN-Spanish], Carbomerum [INN-Latin], Carbopol, Carboxypolymethylene, Carboxypolymethylene resin, 2-Propenoic acid, Acrylic acid, Acroleic acid, Ethylenecarboxylic acid, Propenoic acid, Vinylformic acid, $CH_2=CHCOOH$, Propene acid, Kyselina akrylova, 2-Propenoic acid, calcium salt, Acrylic acid, calcium salt, Calcium acrylate, Calcium diacrylate, acrylic acid, 2-propenoic acid, AIDS-209945, AIDS209945, Carbomer, Carbopol 934P, 2-Propenoic acid, 2-methyl-, 2-hydroxyethyl ester, polymer with etheny-1-acetate and 2-ethylhexyl 2-propenoate.

In an embodiment, pharmaceutically acceptable HX salts of the Nitrogen Mustard alkylating agents used in the treatment of skin disorders may be more stable and have a longer duration of activity because the pharmaceutically acceptable HX salts of the Nitrogen Mustards may be more resistant to attack by water than the respective free base form of the Nitrogen Mustard. In an embodiment, the pharmaceutically acceptable HX salts of the Nitrogen Mustard alkylating agents may be added to a non-aqueous vehicle or carrier that may not include petrolatum. In an embodiment, the use of pharmaceutically acceptable HX salts of the Nitrogen Mustard alkylating agents and/or adding them to the non-aqueous vehicle or carrier that may not include petrolatum may result in greater stability and longer duration of action in the treatment of skin disorders.

In an embodiment, the skin disorder is selected from the group consisting of psoriasis, eczema, actinic keratosis, lupus, sarcoidosis, alopecia, cutaneous T-Cell lymphoma, i.e., mycosis fungoides, lymphoreticular neoplasia, pleural and peritoneal effusions, cutaneous B-cell lymphoma, pseudolymphomas of the skin, squamous cell carcinoma, basal cell carcinoma, bronchogenic carcinoma, malignant melanoma, lymphosarcoma, chronic lymphocytic leukemia, polycythemia vera, lymphomatoid papulosis, Mucha-Habberman's disease (PLEVA), and combinations thereof.

Methods of delivery, as in the step 10 of the method 1 comprise topical administration of the Nitrogen Mustard or Nitrogen Mustard•HCl to humans and animals of sterile solutions or suspensions, wherein the dosage contains suitable quantities of an active ingredient. Topical solutions or suspensions are incorporated in a slow release non-aqueous matrix for administering transdermally. In an embodiment, a dosage for mammals may be from about 0.0001 percent by weight to about 2.0 percent by weight of the active ingredient in the non-aqueous and non-petrolatum matrix per day. In another embodiment, the dosage for mammals may be from about 0.015 percent by weight to about 0.04 percent by weight of the active ingredient in the non-aqueous and non-petrolatum matrix per day. In an embodiment, the dosage for mammals may be from about 0.015 to about 0.030 percent by weight of the active ingredient in the non-aqueous and non-petrolatum matrix per day. Hereinafter, topical administration means applying a drug to a localized area of the body or to the surface of a body part.

In embodiments of the present invention, a method for treating a person with a skin disorder, comprising: topically applying the Nitrogen Mustard or Nitrogen Mustard•HCl to the affected skin. In an embodiment of the method, the non-aqueous vehicle or carrier that does not include petrolatum or ethanol ameliorates skin irritation resulting from the Nitrogen Mustard or its HX salt, by providing an effective dose of the Nitrogen Mustard or Nitrogen Mustard•HCl. Hereinafter, "ameliorates" means to lessen pain and reduce skin irritation, resulting in making an improvement because skin irritation has been reduced. Hereinafter, an effective dose of the Nitrogen Mustard or Nitrogen Mustard•HCl may be sufficient to treat the skin having one of the aforementioned diseases without causing hypersensitivity, as disclosed in Table 1, supra.

In embodiments of the present invention, a method for stabilizing a volatile alkylating agent, comprising: providing a non-aqueous flowable ointment or cream, wherein the non-aqueous flowable ointment or cream does not include petrolatum or ethanol; reconstituting an HX salt of the volatile alkylating agent in anhydrous solvent that does not include ethanol; combining with mixing the non-aqueous flowable ointment or cream and the HX salt of the volatile alkylating agent. In an embodiment, in the method for stabilizing the Nitrogen Mustard or Nitrogen Mustard•HCl, the HX salt of the Nitrogen Mustard is Nitrogen Mustard•HCl. In an embodiment of the method for stabilizing the Nitrogen Mustard or the Nitrogen Mustard•HCl, a duration of activity of the Nitrogen Mustard or the HX salt of the Nitrogen Mustard is from about 3 months to about 3 years.

In an embodiment, in the method for stabilizing the Nitrogen Mustard or the Nitrogen Mustard•HCl, the non-aqueous flowable ointment or cream includes polypropylene glycol (PPG), propylene glycol (PG) or polyethylene glycol (PEG) or ethylene glycol (EG). In an embodiment, in the method for stabilizing the Nitrogen Mustard or the Nitrogen Mustard•HCl, the non-aqueous flowable ointment or cream consists essentially of Propylene Glycol, Ethoxy Diglycol Reagent, Hydroxypropylcellulose, Menthol Crystals USP, Butylated Hydroxytoluene NF, Glycerin USP, Edetate Disodium USP, Decyl Methyl Sulfoxide, and Kris-Ester 236.

In an embodiment, in the method for stabilizing the Nitrogen Mustard or the Nitrogen Mustard•HCl, the Nitrogen Mustard or its HX salt is selected from the group consisting of bis-(2-chloroethyl)ethylamine, bis-(2-chloroethyl)methylamine, tris-(2-chloroethyl)amine, and combinations thereof.

In an embodiment, the acceptable non-aqueous vehicle or carrier that does not include petrolatum or ethanol for the purpose of this invention may be flowable non-aqueous pharmaceutical vehicle or carriers such as creams or ointments that do not contain nucleophiles, e.g., water or ethanol, that may decompose the Nitrogen Mustard or its HX salt, structure IX, as depicted in Reaction 5, supra. In an embodiment, suitable pharmaceutically acceptable carriers include Ethoxy Diglycol Reagent, Hydroxypropylcellulose, Menthol Crystals USP, Butylated Hydroxytoluene NF, Glycerin USP, Edetate Disodium USP, Decyl Methyl Sulfoxide, Kris-Ester 236, Propylene glycol and Ethylene Glycol. In an embodiment, the polypropylene glycol (PPG), propylene glycol (PG), polyethylene glycol (PEG) or ethylene glycol (EG) may be from about 15 to about 60 weight percent propylene glycol or ethylene glycol. The non-aqueous vehicle or carrier that does not include petrolatum or ethanol may also contain adjuvants such as preserving, stabilizing, wetting, emulsifying agents and the like together with the sensitizer of this invention.

In an embodiment of the present invention, the sensitizers can also be used as adjunct therapy in combination with existing therapies, such as hyperthermia, in the management cancer treatment in patients having cancer.

Example 1

Preparation of from about 0.001 to about 2.0 Bis-(2-chloroethyl)methylamine Hydrochloride, Structure IX, as Depicted in Reaction 5 Supra The drug product formulation consists of a pharmaceutically acceptable nitrogen mustard hydrochloride in a topical ointment base that does not include petrolatum or ethanol. The components/compositions are provided in Table 2 that follows, assuming a batch size of 1 liter.

TABLE 2

Unit/Batch Composition

| Ingredient | Amount per 100 ml | Per Batch[a] | Percent |
|---|---|---|---|
| PPG, PG, PEG or EG USP | 15-60 ml | 0.15-0.6 L | 15-60% |
| Ethoxy Diglycol Reagent | 15-60 ml | 0.15-0.6 L | 15-60% |
| Hydroxypropylcellulose NF 1500 CPS | 0.75 gm | 0.0075 kg | 0.75% |
| Menthol Crystals USP | 0.08 gm | 0.0008 kg | 0.08% |
| Butylated Hydroxytoluene NF (BHT) | 0.05 gm | 0.0005 kg | 0.05% |
| Glycerin USP | 12.75 ml | 0.1275 L | 12.75% |
| Edetate Disodium USP | 0.05 gm | 0.0005 kg | 0.05% |
| Decyl Methyl Sulfoxide | 0.125 gm | 0.00125 kg | 0.13% |
| Kris-Ester 236 liquid | 5 gm | 0.05 kg | 5.00% |
| Alchohol Anydrous 100% SDA 3A | 2.175 ml | 0.02175 L | 2.18% |
| Bis-(2-chloroethyl)methylamine HCl[b] | 0.001-2.0 gm gm | 0.00001-0.02 kg | 0.001-2.0% |

[a]Slight overages of the drug substances may be used as required to offset losses during manufacture.
[b]Available from Merck & Co., West Point, PA 19486.

Manufacturing

The drug product, e.g., having 0.001-2.0 percent by weight Nitrogen Mustard as Bis-(2-chloroethyl)methylamine•HCl, structure IX, as in Reaction 5, supra, may be manufactured according to the following general procedure:

Preparation of the Ointment

1. All dry excipient ingredients are assembled and weighed out according to the formula in Table 2 and placed in an appropriate vessel. Hereinafter, an excipient is an inert substance which is added to the free form of the nitrogen mustard or its pharmaceutically acceptable HX salt to provide bulk. Hereinafter, the dry excipient ingredients are indicated as being added as solid weight, such as gram, i.e. gm.
2. Particle sizes of the dry material are reduced to a uniform size through tritration.
3. Polypropylene glycol (PPG), propylene glycol (PG), polyethylene glycol (PEG) or ethylene glycol (EG) from about 15 to about 60 percent by weight is then added via the principle of geometric dilution to form a smooth paste. Once a smooth paste is achieved, the propylene or ethylene glycol continues to be added until a volume that retains a flow like quality is obtained.
4. The entire contents are then transferred to a large beaker. A spin bar is added and the beaker is placed on a magnetic stirring plate and mixing is begun.
5. As the mixture continues to spin, glycerin is added. While the mixture spins, the original vessel is washed with from about 15 to about 60 percent by weight ethoxy diglycol and the contents of the vessel are added to the spinning mixture in the beaker.
6. After the ethoxy diglycol is added, kris-ester is added to the spinning mixture. This mixture then is spun for approximately one to two hours. After the spinning is finished the mixture is covered and left to sit over-night.
7. The next day the mixture is mixed with a high shear mixer to a uniform consistency with minimal to no air. Air and moisture may be removed during mixing by applying a vacuum from about 0.01 to about 0.1 torr The mixture is then brought to ambient pressure by adding dry nitrogen.

Adding the Nitrogen Mustard

8. The appropriate concentration and amount of nitrogen mustard is reconstituted with absolute alcohol (200 proof) then added to the appropriate amount of non-aqueous vehicle or carrier, wherein the non-aqueous vehicle or carrier does not include petrolatum or ethanol and mixed to a uniform consistency via agitation for 60-90 seconds For example, in an embodiment, a concentration in mg/ml of the pharmaceutically acceptable Nitrogen Mustard•HCl in the non-aqueous vehicle or carrier that does not include petrolatum or ethanol is advantageously from about 1 mg of Nitrogen Mustard•HCl per 100 ml of non-aqueous vehicle to about 2000 mg of Nitrogen Mustard•HCl per 100 ml of non-aqueous vehicle. In an embodiment, a concentration in mg/ml of Nitrogen Mustard•HCl in a non-aqueous vehicle or carrier that does not include petrolatum or ethanol is advantageously from about 10 mg of Nitrogen Mustard•HCl per 100 ml of non-aqueous vehicle or carrier that does not include petrolatum or ethanol to about 40 mg of Nitrogen Mustard•HCl per 100 ml of non-aqueous vehicle or carrier that does not include petrolatum or ethanol. In an embodiment, a concentration in mg/ml of Nitrogen Mustard•HCl used in a non-aqueous vehicle or carrier that does not include petrolatum or ethanol is advantageously from about 15 mg of Nitrogen Mustard•HCl per 100 ml of non-aqueous vehicle or carrier that does not include petrolatum or ethanol to about 30 mg of Nitrogen Mustard•HCl per 100 ml of non-aqueous vehicle or carrier that does not include petrolatum or ethanol.
9. This mixture is then poured into a 50 ml flip top plastic cylinder and shipped to the appropriate patient.

Clean-Up

All vessels used in the process are placed in a Sodium Thiosulfate aqueous bath. Contents are left in the bath for 2 hours and then the washed. The bath is then discarded by normal means. Note: Sodium Thiosulfate reacts with nitrogen mustard to create an innocuous, safe mixture that can be discarded by normal means.

Example 2

Preparation of from about 0.001 to about 2.0 Bis-(2-chloroethyl)methylamine Hydrochloride, Structure IX, as Depicted in Reaction 5 Supra The drug product formulation consists of a pharmaceutically acceptable nitrogen mustard hydrochloride in a topical ointment base. The components/compositions are provided in Table 3 that follows, assuming a batch size of 1 liter.

TABLE 3

Unit/Batch Composition

| Ingredient[a] | Parts per 100 Parts by Weight of Free Base Nitrogen Mustard or HX Salt |
|---|---|
| Dimethicone or Cyclomethicone | 10-60 |
| Diethylene Glycol Monosubstituted Ether, DGMSE, $HO(CH_2CH_2O)_2R_{79}$ | 10-16 |
| Hydroxypropylcellulose NF 1500 CPS or buffer gel | 0-5 |
| Menthol Crystals USP | 0-1 |
| Butylated Hydroxytoluene NF (BHT) | 0-1 |
| Glycerin USP | 1-2 |
| Edetate Disodium USP | 0-0.05 |
| Decyl Methyl Sulfoxide | 0-0.125 |
| Kris-Ester 236 liquid | 0-5 |
| Anydrous Secondary or tertiary Alcohol | 1-20 |
| API, e.g., Bis-(2-chloroethyl)methylamine HCl[b] | 0.001-2.0 |
| $C_nH_{(2n+2)}COOH$, (n = 1-6) | 0.01-15 |

[a]Slight overages of the drug substances may be used as required to offset losses during manufacture.
[b]Available from Merck & Co., West Point, PA 19486.

The acceptable non-aqueous vehicle or carrier that does not include petrolatum or ethanol for the purpose of this invention that is the flowable non-aqueous pharmaceutically acceptable non-aqueous vehicle or carrier that does not include petrolatum or ethanol such as creams or ointments do not contain nucleophiles, e.g., water or ethanol, that may decompose the free form of the Nitrogen Mustard or its HX salt, structure IX, as depicted in Reaction 5, supra, may be dimethyl polysiloxane fluid such as dimethicone or cyclomethicone having essentially no moisture content.

Hereinafter dimethicone means low viscosity silicones, low viscosity, i.e. from about 1 cps. to about 1,000 cps at 25° C. polydimethylsiloxanes, Hexamethyldisiloxane, CAS#107-46-0, pure silicone 1 cSt, volatile silicone, volatile silicones, volatile polydimethylsiloxanes, low temperature silicones, skin care silicone, skin care silicones, Octamethyltrisiloxane, CAS#107-51-7, CAS107-51-7, Decamethyltetrasiloxane, (CAS#141-62-8, Dodecamethylpentasiloxane CAS#141-63-9, trisiloxane, low viscosity dimethicone, volatile dimethicone, cosmetic dimethicone fluid, cosmetic base fluids, suntan lotion silicone, antiperspirant silicone, hair care silicone, low surface tension silicone, and low heat of vaporization silicone.

Hereinafter, cyclomethicone means cyclopentasiloxane, volatile poydimethylcyclosiloxane, CAS 541-02-6, CAS#541-02-6, low surface tension silicone, volatile silicone, D5 silicone, Dow Corning 245 fluid, DC 245 fluid, 245 silicone, skin cream silicone, antiperspirant silicone, suntan lotion silicone, silicone for skin, skincare silicone, bodycare silicone, bath oil silicone, GE 1202, GE SF1202 cyclopentasiloxane, D5 Cyclopentasiloxane, and D5 Decamethylcyclo Pentasiloxane.

Generally, dimethicone and cyclomethicone are dimethyl silicone oils with good emollience, strong moisturization and humectant properties. Dimethicone and cyclomethicone have very low moisture content, as water, i.e. <0.1% by weight because they are methyl stopped instead of OH stopped polymers.

Manufacturing

The drug product, e.g., having 0.001-2.0 percent by weight Nitrogen Mustard as Bis-(2-chloroethyl)methylamine•HCl, structure IX, as in Reaction 5, supra, in Dimethicone or Cyclomethicone Ointment may be manufactured according to the following general procedure:

Preparation of the Dimethicone or Cyclomethicone Ointment a) All dry excipient ingredients are assembled and weighed out according to the formula in Table 3 and placed in an appropriate vessel.

b) Particle sizes of the dry material are reduced to a uniform size through tritration.

c) Dimethicone or cyclomethicone from about 10 to about 60 percent by weight is then added via the principle of geometric dilution to form a smooth paste. Once a smooth paste is achieved, the Dimethicone or cyclomethicone continues to be added until a volume that retains a flow like quality is obtained.

d) The entire contents are then transferred to a large beaker. A spin bar is added and the beaker is placed on a magnetic stirring plate and mixing is begun.

e) As the mixture continues to spin, glycerin is added. While the mixture spins, the original vessel is washed with from about 10 to about 16 percent by weight ethoxy diglycol and the contents of the vessel are added to the spinning mixture in the beaker.

f) After the ethoxy diglycol is added, from about 0.01-15 percent by weight of a pH modifier such as citric acid, lactic acid or aliphatic acids having a formula $C_nH_{(2n+2)}COOH$, (n=1-6) is added to the spinning mixture. This mixture then is spun for approximately one to two hours. After the spinning is finished the mixture is covered and left to sit over-night.

g) The next day the mixture is mixed with a high shear mixer to a uniform consistency with minimal to no air. Air and moisture may be removed during mixing by applying a vacuum from about 0.01 to about 0.1 torr. The mixture is then brought to ambient pressure by adding dry nitrogen. Combining the Nitrogen Mustard and the Dimethicone or Cyclomethicone Non-Aqueous Vehicle or Carrier that does not Include Petrolatum or Ethanol of Step g) Supra.

In one embodiment, a pharmaceutically acceptable nitrogen mustard•HCl having an essentially completely uniform consistency may be formed by agitating for 60-90 seconds using a high shear mixer to mix 1) an appropriate amount of API having been be reconstituted with an anhydrous secondary or tertiary alcohol such as isopropyl alcohol, wherein ethanol has been rigorously excluded from the anhydrous secondary or tertiary alcohol such as isopropyl alcohol, and 2) the appropriate amount of non-aqueous vehicle or carrier that does not include petrolatum or ethanol from step g), supra, wherein the non-aqueous vehicle or carrier does not include petrolatum or ethanol. For example, in an embodiment, a concentration in mg/ml of the pharmaceutically acceptable Nitrogen Mustard•HCl in the non-aqueous vehicle or carrier that does not include petrolatum or ethanol is advantageously from about 1 mg of Nitrogen Mustard•HCl per 100 ml of non-aqueous vehicle to about 2000 mg of Nitrogen Mustard•HCl per 100 ml of non-aqueous vehicle. In another embodiment, a concentration in mg/ml of the pharmaceutically acceptable Nitrogen Mustard•HCl used in a non-aqueous vehicle or carrier that does not include petrolatum or ethanol is advantageously from about 10 mg of Nitrogen Mustard•HCl per 100 ml of non-aqueous vehicle or carrier that does not include petrolatum or ethanol to about 40 mg of Nitrogen Mustard•HCl per 100 ml of non-aqueous vehicle or carrier that does not include petrolatum or ethanol. In another embodiment, a concentration in mg/ml of the pharmaceutically acceptable Nitrogen Mustard•HCl used in a non-aqueous vehicle or carrier that does not include petrolatum or ethanol is advantageously from about 15 mg of Nitrogen Mustard•HCl per 100 ml of non-aqueous vehicle or carrier that does not include petrolatum or ethanol to about 30 mg of Nitrogen Mustard•HCl per 100 ml of non-aqueous vehicle or carrier that does not include petrolatum or ethanol. This mixture may then be poured into a 50 ml flip top plastic cylinder and shipped to the appropriate patient.

The inventors disclose that lower volume containers having from about 0.01 to about 0.2 ml, from about 0.1 to about 0.5 ml, or from about 0.1 to about 1 ml may advantageously be used to provide from 1 to 10 applications of the pharmaceutically acceptable Nitrogen Mustard•HCl over a shorter period of use than the 50 ml flip top plastic cylinders, so that lower amounts of nucleophiles such as ambient water or other ambient nucleophiles such as methanol or ethanol may be introduced into the lower volume containers than when the flip top plastic cylinder is opened to the ambient environment over a period of 100 to 1000 applications. The inventors anticipate decreased decomposition of the free form nitrogen mustard or its HX salt, structure IX, depicted in Reaction 5, supra, when the pharmaceutically acceptable nitrogen mustard is contained in lower volume containers intended for from about 1 to 10 applications. In theory, the chlorides of the free form of the nitrogen mustard or its HX salt may be displaced by nucleophilic attack, such as by water or ethanol, resulting in substitution of the Cl by an OH. Said decomposition of the free form of the nitrogen mustard or its HX salt may be avoided by isolating the nitrogen mustard from traces of water, ethanol or other nucleophiles in the environment. An apparatus 20, as depicted in FIG. 2, infra, depicts this smaller volume container.

Figure 2:
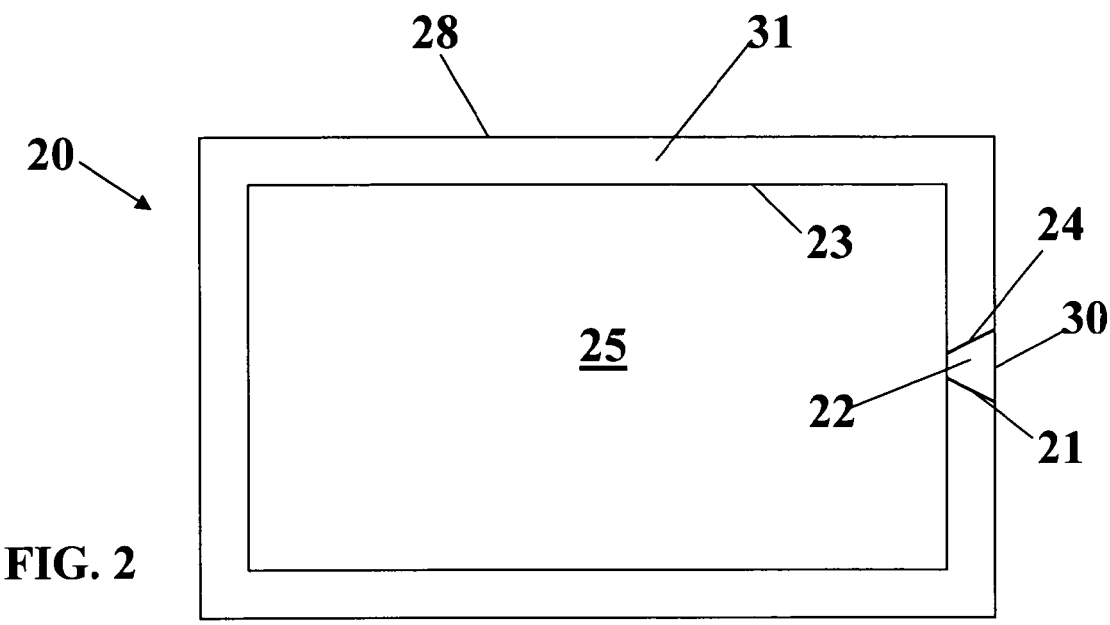
FIG. 2 depicts a front cross-sectional view of an apparatus having a compartment partially enclosed by a wall, in accordance with embodiments of the present invention.

FIG. 2 depicts a front cross-sectional view of the apparatus 20 for containing the pharmaceutically acceptable Nitrogen Mustard•HCl in the non-aqueous vehicle or carrier that does not include petrolatum or ethanol or the stabilized volatile alkylating agent or HX salt of the stabilized volatile alkylating agent, comprising: a compartment 25 enclosed by a wall 31. The wall 31 comprises an outer surface 28 and an inner surface 23, ends 24 and 21, and opening 30. The first compartment 25 may be charged with the essentially completely uniform mixture of the pharmaceutically acceptable nitrogen mustard•HCl, supra, through the opening 30. The opening 30 may be closed with plug 22. The plug 22 may be made of the same material as the wall 31, or a lower melting plastic or wax material.

Figure 3:
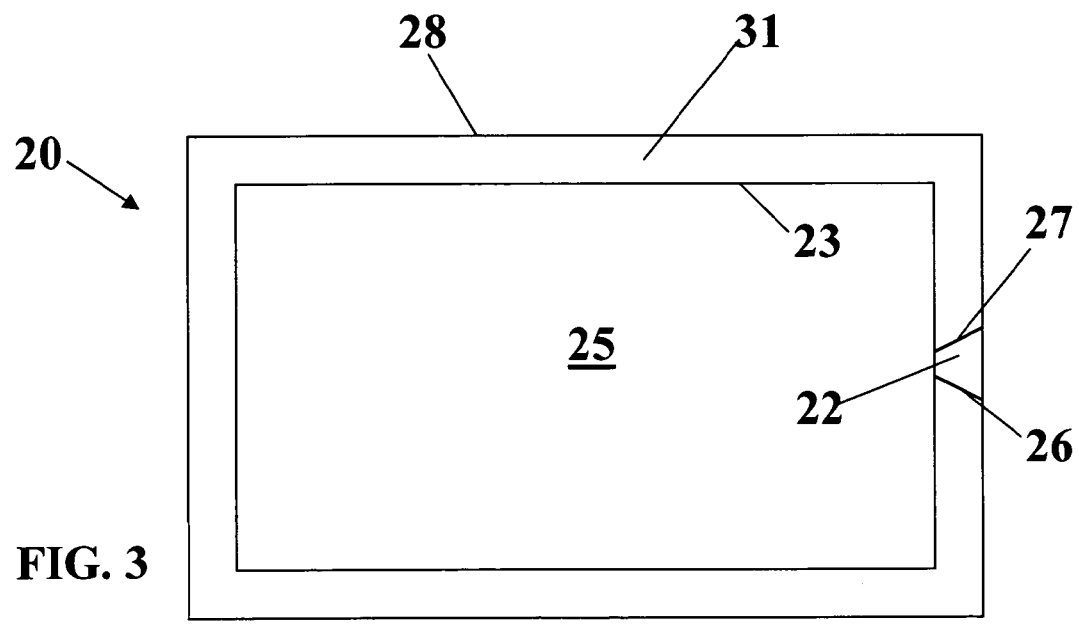
FIG. 3 depicts the apparatus having plugs mechanically sealed to close an opening in the wall, in accordance with embodiments of the present invention.

FIG. 3 depicts the apparatus 20, after forming heat seals 26 and 27 by heating the plug 22 and the ends 21 and 24 to their melting points, wherein heating physically and mechanically couples ends 21 and 24 to form mechanically strong heat seals 26 and 27.

Figure 4:
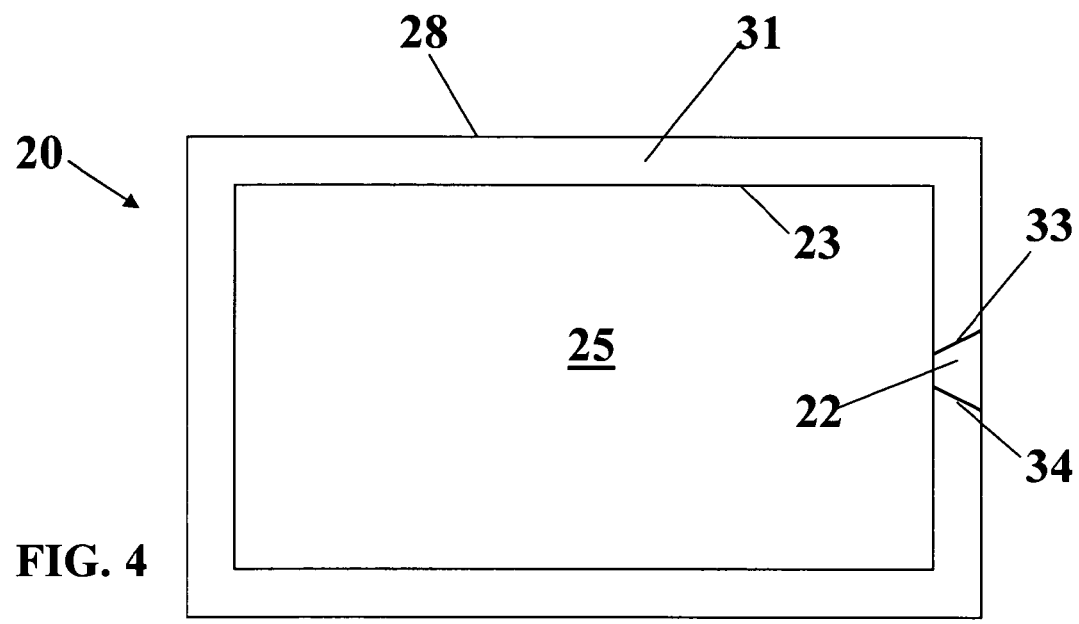
FIG. 4 depicts the apparatus wherein the heat seals have been serrated to permit easy removal of the plugs, in accordance with embodiments of the present invention.

FIG. 4 depicts the apparatus 20, after forming serated perforations 33 and 34 in the plug 22 using a crimping tool or other appropriate device for forming serated perforations 33 and 34. The serated perforations 33 and 34 weaken the heat seals 21 and 24 so that they become mechanically less strong, resulting in a tear line for removal of the plug 22 by the patient seeking to apply the pharmaceutically acceptable nitrogen mustard•HCl to a diseased area or area for treatment. Alternatively, a person could use an instrument having a sharp edge or blade, such as scissors, a razor blade or a knife, to pierce the plug 22, thereby restoring the opening 30 in the wall 31 of the apparatus 20.

In one embodiment, a person wishing to apply the pharmaceutically acceptable nitrogen mustard•HCl to the diseased area or area for treatment may remove plug 22 from the wall 31 of the apparatus 20, restoring the opening 30 in the wall 31. A person squeezing or applying pressure to the wall 31 reduces the volume of the compartment 25, causing the pharmaceutically acceptable nitrogen mustard•HCl to flow out of the compartment 25 through the opening 30, thereby enabling topical application of the pharmaceutically acceptable nitrogen mustard•HCl to a diseased area or area for treatment.

In one embodiment, a concentration of the pharmaceutically acceptable Nitrogen Mustard•HCl in the non-aqueous vehicle or carrier that does not include petrolatum or ethanol in the compartment 25 is from about 1 mg of Nitrogen Mustard•HCl per 100 ml of non-aqueous vehicle to about 2000 mg of Nitrogen Mustard•HCl per 100 ml of non-aqueous vehicle. In another embodiment, a concentration of the pharmaceutically acceptable Nitrogen Mustard•HCl in the non-aqueous vehicle or carrier that does not include petrolatum or ethanol is from about 10 mg of Nitrogen Mustard•HCl per 100 ml of non-aqueous vehicle or carrier that does not include petrolatum or ethanol to about 40 mg of Nitrogen Mustard•HCl per 100 ml of non-aqueous vehicle or carrier that does not include petrolatum or ethanol. In another embodiment, a concentration of the pharmaceutically acceptable Nitrogen Mustard•HCl in the non-aqueous vehicle or carrier that does not include petrolatum or ethanol is advantageously from about 15 mg of Nitrogen Mustard•HCl per 100 ml of non-aqueous vehicle or carrier that does not include petrolatum or ethanol to about 30 mg of Nitrogen Mustard•HCl per 100 ml of non-aqueous vehicle or carrier that does not include petrolatum or ethanol. An orifice or opening 30 may be made by forming an opening in the outer wall 31, through which opening 30 this mixture of the Nitrogen Mustard is then provided by prescription of a physician for treatment of the patient.

The outer wall 31 of apparatus 20 is impermeable or impervious to the mixture of step g) or step 9), supra, and/or the reconstituted nitrogen mustard solutions. Hereinafter, "impermeable" or "impervious" means the wall 31 prevents the mixture of step g) or step 9), supra, and/or the reconstituted nitrogen mustard solutions to pass or diffuse through the wall 31. Hereinafter "impervious" means not admitting of passage of the mixture of step g) or step 9), supra, and/or the reconstituted nitrogen mustard solutions through the wall 31 or the wall 31 being capable of being affected by the mixture of step g) or step 9), supra, and/or the reconstituted nitrogen mustard solutions. The wall 31 may be made from aluminum foil, plastic lined or resin coated aluminum foil, elastomeric materials including ethylene/propylene copolymers, ethylene/ethylacrylate copolymers, ethylene/vinyl acetate copolymers, silicone elastomers, medical-grade polydimethylsiloxanes, neoprene rubber, polyisobutylene, chlorinated polyethylene, polyvinyl chloride, vinylchloride-vinyl acetate copolymer, polymethacrylate polymer (hydrogel), polyvinylidene chloride, poly(ethylene terephthalate), butyl rubber, epichlorohydrin rubbers, ethylene-vinyl alcohol copolymer, ethylenevinyloxyethanol copolymer; silicone copolymers, polysiloxane-polycarbonate copolymers, polysiloxane-polyethyleneoxide copolymers, polysiloxane-polymethacrylate copolymers, polysiloxane-polymethacrylate copolymers, polysiloxane-alkylene copolymers polysiloxane-ethylene copolymers, polysiloxane-alkylenesilane copolymers, polysiloxaneethylenesilane copolymers, cellulose polymers, methyl cellulose, ethyl cellulose, hydroxypropyl methyl cellulose, cellulose esters, polycarbonates, polyesters, polytetrafluoroethylene, starches, gelatins, natural gums, synthetic gums, and combinations thereof.

Clean-Up

All vessels used in the process are placed in a Sodium Thiosulfate aqueous bath. Contents are left in the bath for 2 hours and then the washed. The bath is then discarded by normal means. Note: Sodium Thiosulfate reacts with nitrogen mustard to create an innocuous, safe mixture that can be discarded by normal means.

The foregoing description of the embodiments of this invention has been presented for purposes of illustration and description. It is not intended to be exhaustive or to limit the invention to the precise form disclosed, and obviously, many modifications and variations are possible.

We claim:

1. A method for treating a person with a skin disorder, comprising topically applying to the affected skin a non-aqueous composition comprising: (a) bis-(2-chloroethyl)methylamine or a pharmaceutically acceptable salt thereof; and (b) a pharmaceutically acceptable excipient, wherein:
the bis-(2-chloroethyl)methylamine or pharmaceutically acceptable salt thereof is present in an amount of about 0.001% to about 2.0% by weight of the composition;
the pharmaceutically acceptable excipient is a compound of the formula $HOCH_2CH_2OCH_2CH_2OR_{79}$, wherein $R_{79}$ is a linear alkyl group having 1-6 carbon atoms; and
the skin disorder is psoriasis, mycosis fungoides, or alopecia.

2. The method of claim 1, wherein the bis-(2-chloroethyl)methylamine is in the form of an acid-addition or base-addition salt.

3. The method of claim 2, wherein the acid-addition salt is an HCl, HBr, HI, $H_2SO_4$, or $HNO_3$ salt.

4. The method of claim 1, wherein the pharmaceutically acceptable excipient is a compound of the formula $HOCH_2CH_2OCH_2CH_2OR_{79}$, wherein $R_{79}$ is a linear alkyl group having 2 carbon atoms (ethoxy diglycol reagent).

5. The method of claim 1, wherein the bis-(2-chloroethyl)methylamine or pharmaceutically acceptable salt thereof is present in an amount of about 0.01% to about 0.04% by weight of the composition.

6. The method of claim 2, wherein the acid-addition salt is an HCl salt.

7. The method of claim 6, wherein the pharmaceutically acceptable excipient is a compound of the formula $HOCH_2CH_2OCH_2CH_2OR_{79}$, wherein $R_{79}$ is a linear alkyl group having 2 carbon atoms (ethoxy diglycol reagent).

8. The method of claim 1, wherein the skin disorder is mycosis fungoides.

9. The method of claim 1, wherein the skin disorder is psoriasis.

10. The method of claim 1, wherein the skin disorder is alopecia.

* * * * *